United States Patent
Chiu et al.

(10) Patent No.: US 11,406,673 B2
(45) Date of Patent: Aug. 9, 2022

(54) **COMPOSITION HAVING *BACILLUS COAGULANS* TCI711 AND METHOD FOR SOBERING UP BY USING THE SAME**

(71) Applicant: TCI CO., LTD., Taipei (TW)

(72) Inventors: Yu-Kai Chiu, Taipei (TW); Yung-Hsiang Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/993,284

(22) Filed: Aug. 14, 2020

(65) Prior Publication Data

US 2021/0046126 A1    Feb. 18, 2021

Related U.S. Application Data

(60) Provisional application No. 62/886,653, filed on Aug. 14, 2019.

(51) Int. Cl.
| | | |
|---|---|---|
| *A61K 39/07* | (2006.01) | |
| *A61K 35/742* | (2015.01) | |
| *A61K 35/00* | (2006.01) | |
| *A61P 1/16* | (2006.01) | |

(52) U.S. Cl.
CPC ............ *A61K 35/742* (2013.01); *A61K 39/07* (2013.01); *A61P 1/16* (2018.01); *A61K 2035/115* (2013.01)

(58) Field of Classification Search
None
See application file for complete search history.

(56) References Cited

FOREIGN PATENT DOCUMENTS

| CN | 109007676 A | 12/2018 |
|---|---|---|
| TW | I669124 B | 8/2019 |

OTHER PUBLICATIONS

Search report dated Jul. 9, 2021, listed in correspondent Taiwan patent application No. 109127834 (publication No. TW 202106317). Probiotic Bacillus coagulans MTCC 5856 spores exhibit excellent in-vitro functional efficacy in simulated gastric survival, mucosal adhesion and immunomodulation., Shinde et al., Journal of Functional Foods, vol. 52, Jan. 2019, pp. 100-108. Full text, section 2.2 Tolerance of B. coagulans spores to in-vitro simulated digestion in p. 101, 1st paragraph in the right column of p. 104, 1st paragraph in the right column of p. 105.

*Primary Examiner* — Sarvamangala Devi
(74) *Attorney, Agent, or Firm* — Chieh-Mei Wang

(57) ABSTRACT

A method of sobering up, comprising administering composition comprising an effective amount of *Bacillus coagulans* TCI711. The *Bacillus coagulans* TCI711 is deposited in Consortium Food Industry Research and Development Institute (Deposit number: BCRC910807) and German Microbial and Cell Culture Collection Center (DSMZ-DEUTSCHE SAMMLUNG VON MIKROORGANISMEN UND ZELLKULTUREN GmbH) (Deposit number: DSM33163).

7 Claims, 5 Drawing Sheets

COMPOSITION HAVING BACILLUS COAGULANS TCI711 AND METHOD FOR SOBERING UP BY USING THE SAME

CROSS-REFERENCE TO RELATED APPLICATION

This application claims the benefit of U.S. provisional application Ser. No. 62/886,653 filed on Aug. 14, 2019. The entirety of the above-mentioned patent applications are hereby incorporated by references herein and made a part of the specification.

BACKGROUND

Technical Field

The present invention relates to *Bacillus coagulans*, more particularly to a method of sobering up, comprising administering a composition comprising an effective dose of *Bacillus coagulans* TCI711.

Related Art

Modern people, for social contact or personal preference, often encounter with alcohol drinking conditions. After drinking, in the human body, most of alcohol will be absorbed in the front half section of the intestinal tract, and the absorbed alcohol is guided to the livers and metabolized into acetaldehyde. In the case of a small amount of acetaldehyde, most of the acetaldehyde can be successfully metabolized to acetic acid, and can finally become carbon dioxide and water to be discharged out of the body.

However, excessive acetaldehyde will cause various unrecoverable harm to the human body if it cannot be metabolized in time. The acetaldehyde is a well-known grade 1 carcinogenic substance. After alcohol drinking, more than 90% of alcohol metabolites need to be treated through the livers. Therefore, various kinds of liver injury are often caused by excessive alcohol drinking.

SUMMARY

In a Taiwan patent with a publication number of TWI669124B, the inventor has disclosed a use of *Bacillus coagulans* TCI711 in preparing compositions for metabolizing heavy metal. Additionally, experiments are provided for proving that the *Bacillus coagulans* TCI711 can improve the anti-oxidization ability of the liver cells under general conditions. The *Bacillus coagulans* TCI711 can also improve the mitochondrion activity of the liver cells. The *Bacillus coagulans* TCI711 has the capability of reducing the fatty liver forming possibility. However, in order to improve the value of the *Bacillus coagulans* TCI711, the inventor continuously studies and develops other uses of the *Bacillus coagulans* TCI711 or relevant products thereof.

In view of this, the present invention provides a method of sobering up, comprising administering a composition comprising an effective dose of *Bacillus coagulans* TCI711 and a food, a health food or a diet dietary supplement containing the composition for sobering up.

In some embodiments, a method of sobering up, comprising administering a composition comprising an effective dose of *Bacillus coagulans* TCI711 is provided. The *Bacillus coagulans* TCI711 is deposited in Consortium Food Industry Research and Development Institute (Deposit number: BCRC910807) and German Microbial and Cell Culture Collection Center (DSMZ-DEUTSCHE SAMMLUNG VON MIKROORGANISMEN UND ZELLKULTUREN GmbH) (Deposit number: DSM33163).

In some embodiments, the *Bacillus coagulans* TCI711 includes various enzymes or proteins, including more than 1% of alcohol dehydrogenase and more than 4% of aldehyde dehydrogenase.

In some embodiments, the *Bacillus coagulans* reduces alcohol absorption by forming a protection film on the intestinal wall, so as to achieve a sobering up function.

In some embodiments, the *Bacillus coagulans* achieves a sobering up function by improving the mitochondrion activity of the liver cells. The mitochondrion provides chemical energy for various metabolizing activities of liver cells. When the activity of the mitochondrion in the liver cells is improved, the metabolizing function of the liver cells on the alcohol can also be improved together.

In some embodiments, the *Bacillus coagulans* has acid-alkali tolerance ranging from pH 3 to pH 7.

In some embodiments, the *Bacillus coagulans* has an intestinal tract colonization rate of 346 CFU per intestinal tract cell.

In some embodiments, the effective dose is $1 \times 10^{10}$ cells/day.

In some embodiments, a food product for sobering up includes an effective dose of the *Bacillus coagulans* TCI711. The *Bacillus coagulans* TCI711 has deposit numbers of BCRC910807 and DSM33163.

In some embodiments, the *Bacillus coagulans* TCI711 in the above food product has an effective dose of $1 \times 10^{10}$ cells/day.

Based on the above, the *Bacillus coagulans* TCI711 or a metabolic product thereof according to any one embodiment may be used for preparing compositions for sobering up. In other words, the above compositions have one or more of the following functions: sobering up to protect the livers, reducing alcohol absorption and improving the metabolizing ability of the liver cells. The *Bacillus coagulans* according to any one embodiment directly metabolizes alcohol in contact with the *Bacillus coagulans* through alcohol dehydrogenase and aldehyde dehydrogenase. The *Bacillus coagulans* according to any one embodiment may smoothly tolerate gastric acid to reach the intestinal tract by virtue of its high acid-alkali tolerance. The *Bacillus coagulans* according to any one embodiment may form a protection film on the intestinal tract wall by virtue of its high colonization rate, so as to reduce the absorption amount of the small intestines on the alcohol. The *Bacillus coagulans* according to any one embodiment can effectively improve the metabolizing speed of the alcohol in the body only through being taken at a dose of $1 \times 10^{10}$ cells.

DETAILED DESCRIPTION

Figure 1:
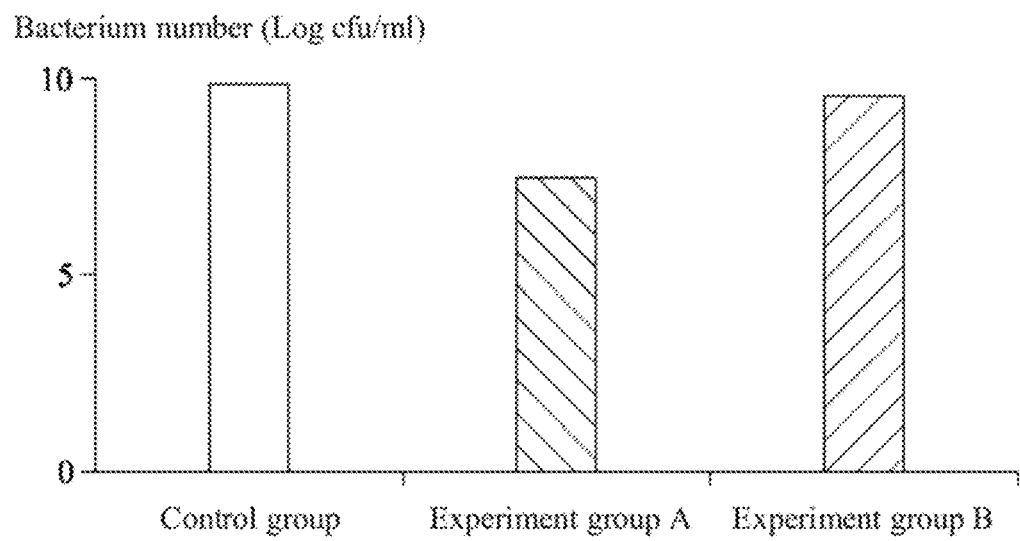
FIG. 1 is a diagram of a result of a gastrointestinal tract digestion simulation experiment.

In an embodiment, *Bacillus coagulans* TCI711 is a gram-positive bacterium capable of generating lactic acid, may grow in an anaerobic environment, and is a facultative anaerobic lactic acid bacterium. The *Bacillus coagulans* may generate endospores in a poor growth environment (for example, exceeding 50° C.) to stop growth. When the endospores react with gastric acid after being eaten and then enter the small intestines, the endospores may be recovered from the spore state to continuously grow and breed in the small intestines, so that the *Bacillus coagulans* TCI711 has the characteristics of acid tolerance and heat tolerance in the spore state.

In some embodiments, the *Bacillus coagulans* TCI711 may be used for preparing compositions for sobering up. Additionally, in some other embodiments, a food product containing the *Bacillus coagulans* TCI711 has a sobering up function.

In some embodiments, the *Bacillus coagulans* TCI711 may directly metabolize alcohol.

In some embodiments, the *Bacillus coagulans* TCI711 includes various enzymes or proteins, such as a 50S ribosomal protein, a small acid-soluble spore protein, a 30S ribosomal protein, an Elongation factor Tu, glyceraldehyde-3-phosphate, aldehyde dehydrogenase, an uncharacterized protein, an ornithine aminotransferase, a ribosome hibernation promoting factor, short-chain dehydrogenase, Pfpl family intracellular protease, succinate CoA ligase, dihydrolipoamide acetyltransferase, 3-oxoacyl-[acyl-carrier protein] reductase, a UPF0180 protein HMPREF3212_01356, a late embryogeneis abundant protein, glucokinase, fructose-1,6-bisphosphatase, a dihydrolipoyllysine-residue, a cold shock protein CspB, aldolase 2, and alcohol dehydrogenase. The alcohol dehydrogenase accounting for more than 1% of the total protein content of the *Bacillus coagulans* TCI711 and the aldehyde dehydrogenase accounting for more than 4% of the total protein content of the *Bacillus coagulans* TCI711 are included.

In some embodiments, the *Bacillus coagulans* TCI711 has a gastric acid and cholate tolerance function. For example, the *Bacillus coagulans* TCI711 has a survival rate of 70% in a stomach simulation environment (pH 3), and a survival rate of 90% in an intestinal tract simulation environment (pH 7).

In some embodiments, the *Bacillus coagulans* TCI711 may realize colonization growth in the human body gastrointestinal tract environment to further form a protection film state on the intestinal wall. Therefore, the *Bacillus coagulans* TCI711 may effectively reduce an absorption rate of the intestinal wall on the alcohol, and the harm of alcohol drinking to the human body is reduced.

In some embodiments, the *Bacillus coagulans* TCI711 has an effective dose of $1 \times 10^{10}$ cells/day.

In some embodiments, the above compositions include a specific content of the *Bacillus coagulans* TCI711.

In some embodiments, the above compositions may be pharmaceutical products.

In other words, the pharmaceutical products include an effective dose of the *Bacillus coagulans* TCI711.

In some embodiments, the above pharmaceutical products may be manufactured into an administration dose form suitable for being taken enterally, parenterally, orally, or topically by using a technology detailly known by those skilled in the art.

In some embodiments, the administration dose form suitable for being taken enterally or orally may be, but is not limited to a tablet, a troche, a lozenge, a pill, a capsule, dispersible powder or granules, a solution, a suspension, an emulsion, syrup, an elixir, slurry or an analogue. In some embodiments, the administration dose form suitable for being taken parenterally or topically may be, but is not limited to an injection, sterile powder, an external preparation or an analogue. In some embodiments, an administration mode of the injection may be subcutaneous injection, intraepidermal injection, intradermal injection or intralesional injection.

In some embodiments, the above pharmaceutical products may include a pharmaceutically acceptable carrier widely used for drug manufacturing technology. In some embodiments, the pharmaceutically acceptable carrier may be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome and an analogue. The types and the quantity of the selected and used carriers fall within the professional quality and routine technology scope of those skilled in the art. In some embodiments, the solvent used as the pharmaceutically acceptable carrier may be water, normal saline, phosphate buffered saline (PBS), or an aqueous solution containing alcohol.

In some embodiments, the above food product includes a specific content of the *Bacillus coagulans* TCI711.

In some embodiments, the food product can be an ordinary food, a health food or a diet dietary supplement. In other words, the ordinary food, the health food or the diet dietary supplement includes an effective dose of the *Bacillus coagulans* TCI711.

In some embodiments, the above food products may be manufactured into a dose form suitable for being taken orally by a technology detailly known by those skilled in the art. In some embodiments, the above ordinary food may be the food product itself or is another food additive. In some embodiments, the ordinary food may be, but is not limited to beverages, fermented foods, bakery products or seasonings.

Experiment 1: Activation of Strain

Firstly, the *Bacillus coagulans* TCI711 (BCRC910807 or DSM33163) stored in glycidol was inoculated into the MRS culture medium (BD Difco™ Lactobacilli MRS Broth, 1% (v/v)), and was cultured over the night in a 37° C. anaerobic environment. The single colony formation was confirmed, so as to obtain the primarily activated *Bacillus coagulans* TCI711.

Then, a proper number of bacterial colonies of the primarily activated *Bacillus coagulans* TCI711 were selected to be cultured in a 15 mL of MRS culture medium, and were cultured over the night in a 37° C. anaerobic environment, so as to form a bacterial solution containing secondarily activated *Bacillus coagulans* TCI711 (called as a secondarily activated bacterial solution for short hereafter).

Experiment 2: Gastrointestinal Tract Digestion Simulation Experiment

The *Bacillus coagulans* TCI711 was tested in three kinds of to-be-tested solutions of simulated gastric acid (pH 3)

(Experiment group A), simulated bile (pH 7) (Experiment group B) and a buffer solution (pH 7) (Control group), so as to conform the acid-alkali tolerance of the *Bacillus coagulans* TCI711 in the organism digestion tract.

A to-be-tested solution adopted in Experiment group A was a potassium chloride buffer solution (0.2M KCL/HCL buffer) with a concentration of 0.2 mol, and the pH was 3. A to-be-tested solution adopted in Experiment group B was potassium chloride (0.2M KCL/HCL buffer) with a concentration of 0.2 mol including 0.3 wt % of cholate (purchased from Difco™ Oxgall, model: 212820), and the pH was 7. A to-be-tested solution adopted in Control group was a potassium chloride (0.2M KCL/HCL buffer) with a concentration of 0.2 mol, and the pH was 7.

A bacterial solution containing the *Bacillus coagulans* TCI711 (called as 1OD bacterial solution hereafter) realizing $OD_{600}$=1 OD (1 OD=$5 \times 10^8$ CFU) was prepared from the secondarily activated bacterial solution prepared in Experiment 1 and the MRS culture medium. $OD_{600}$ was an optical density (OD value) determined by an ELISA reader at a wavelength of 600 nm.

100 μL of the 1OD bacterial solution was taken, and 9.9 mL of the to-be-tested solution was inoculated with the 1OD bacterial solution. Then, the bacterial solution and the to-be-tested solution were sufficiently mixed, and were cultured for 3 h in a 37° C. anaerobic environment so as to form a to-be-tested bacterial solution. 1 mL of the to-be-tested solution was taken to be subjected to sequence multiple dilution (for example, 107 to 10 times). Then, the diluted to-be-tested bacterial solution was cultured for 48 h in a 37° C. anaerobic environment by the MRS culture medium. Next, the bacterium number of the *Bacillus coagulans* TCI711 in each group was calculated by a plate count method.

Referring to FIG. 1, in the figure, the viability of the *Bacillus coagulans* TCI711 was the living bacterium number after counting, and was represented by log CFU/mL. The log CFU/mL represented a colony-forming unit (CFU) contained in per mL of bacterial solution, and was represented by log. From FIG. 1, it could be known that the viability of the *Bacillus coagulans* TCI711 in Control group was 9.88 log CFU/mL, the viability of the *Bacillus coagulans* TCI711 in Experiment group A was 7.48 log CFU/mL, and the viability of the *Bacillus coagulans* TCI711 in Experiment group B was 9.58 log CFU/mL.

Therefore, it could be known that in comparison with Control group, the survival rate of the *Bacillus coagulans* TCI711 was 70% or higher. In other words, the *Bacillus coagulans* TCI711 could survive in a stomach simulation environment (pH 3-4). In comparison with Control group, the survival rate of the *Bacillus coagulans* TCI711 was 90% or higher. In other words, the *Bacillus coagulans* TCI711 could also survive in an intestinal tract simulation environment (pH 7). Therefore, the *Bacillus coagulans* TCI711 had a function of gastric acid and cholate tolerance.

Experiment 3: Intestinal Tract Colonization Experiment

Herein, after human colon cells C2BBel (ATCC® CRL-2102™) and the *Bacillus coagulans* TCI711 were co-cultured, their colonization state was observed by a microscope, and a colonization rate was analyzed by a plate count method, so as to determine the intestinal tract colonization state of the *Bacillus coagulans* TCI711. The intestinal tract is the greatest digestion and absorption organ in the human body. If a probiotic bacterium has a high intestinal tract colonization rate, its efficacies can be more efficiently achieved.

Firstly, a six-well culture tray was taken. The human colon cells were colonized into wells according to a quantity of $7.5 \times 10^5$ cells/well. Additionally, 2 mL of culture solution was added into each well. The material was put into an incubator with a carbon dioxide concentration of 5% and a temperature of 37° C. to be cultured for 24 h. Herein, the culture solution was prepared by adding 10% fetal calf serum (Gibco™, Cat. 10438-026), 1% penicillin/streptomycin (Gibco™, Cat. 15140-122) and 0.01 mg/ml transferrin into a DMEM culture medium (Dulbecco's Modified Eagle Medium, Gibco™, Cat. 12100-038).

Then, a bacterial solution containing the *Bacillus coagulans* TCI711 (called as 1OD bacterial solution hereafter) realizing $OD_{600}$=1 OD (1 OD=$5 \times 10^8$ CFU) was prepared from the secondarily activated bacterial solution prepared in Experiment 1 and the MRS culture medium. $OD_{600}$ was an optical density (OD value) determined by an ELISA reader at a wavelength of 600 nm. The 1OD bacterial solution was centrifuged to collect *Bacillus coagulans* TCI711 thalli. Then, collected thalli were regulated into $10^8$ CFU/ml of bacterial solution for experiment by an antibiotic-free C2BBel culture medium.

After the culture solution in the culture tray was removed, cleaning was performed with 1×PBS (purchased from Gibco™). After the cleaning, for Experiment group 01 and Experiment group 02, 1 mL of bacterial solution for experiment was added in each well. For Control group 01 and Control group 02, 1 mL of C2BBel culture medium (containing no antibiotic and no bacterial solution for experiment) was added into each well. Then, all groups were cultured for 1 h in a low oxygen environment (the oxygen content was less than 1%) at the same time.

After the culture for 1 h, and after supernatants in the culture tray were removed, cleaning was performed for five times with 2 mL of 1×PBS.

Figure 2:
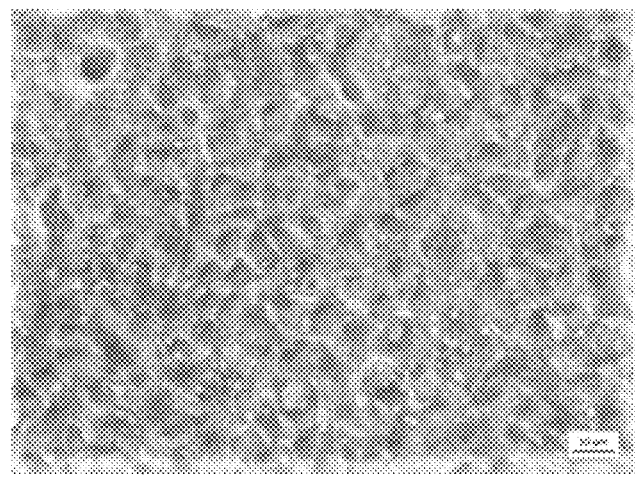
FIG. 2 is a diagram of a growth state of human colon cells.
Figure 3:
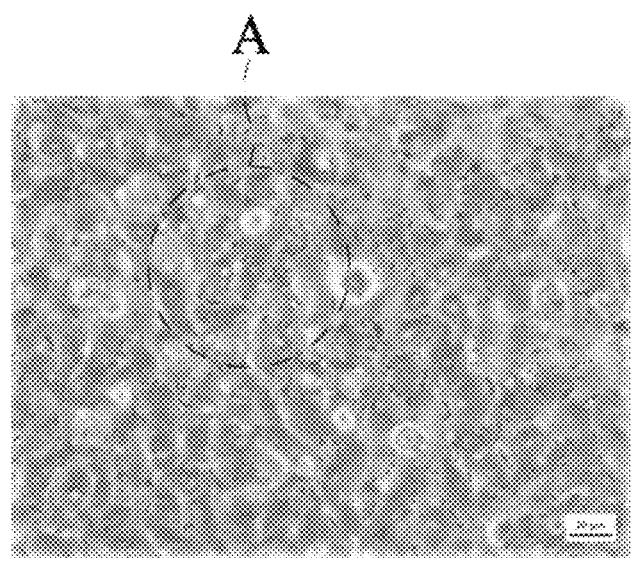
FIG. 3 is a diagram of a state of *Bacillus coagulans* TCI711 colonized in the human colon cells.
Figure 4:
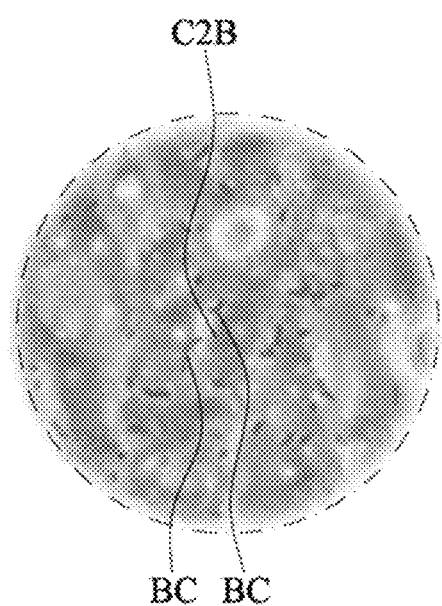
FIG. 4 is a partial enlarged diagram of Part A in FIG. 3.

Then, the human colon cells and the *Bacillus coagulans* TCI711 in Experiment group 01 and Control group 01 were subjected to gram staining (a staining reagent was purchased from BaCO Biotech). Then, Experiment group 01 and Control group 01 were put under a microscope to observe their cell and thallus colonization conditions, as shown in FIG. 2, FIG. 3 and FIG. 4. For Experiment group 02 and Control group 02, 1 mL of Triton® X-100 (nonionic surfactant) was added into each well, and reaction was performed for 10 min at a room temperature so as to take down the human colon cells and the *Bacillus coagulans* TCI711 from the culture tray. Then, tray coating was performed on an agaropectin plate by a dilution smearing method. The colonization rate was analyzed by a plate count method.

Referring to FIG. 2, FIG. 3 and FIG. 4, in comparison with Control group 01, through a photo of Experiment group 01, it could be seen that lots of the *Bacillus coagulans* TCI711 (i.e., tiny and dark color slender shadow BC in FIG. 4) existed on the peripheries of the human colon cells (i.e., oval slightly protruded shadows C2B in FIG. 4), and this was a form of the *Bacillus coagulans* TCI711 colonized on the human colon cells. Additionally, through plate coating counting, it could be obtained that the colonization rate of the *Bacillus coagulans* TCI711 was 346 CFU/cells. It could be known that the *Bacillus coagulans* TCI711 could be stably colonized on the peripheries of the human colon cells.

Experiment 4: Alcohol Metabolizing Experiment

Herein, after an alcohol-containing MRS culture medium was inoculated with the activated *Bacillus coagulans*

TCI711 for a period of time, the change of the alcohol content was measured, so as to determine whether the *Bacillus coagulans* TCI711 has the capability of directly decomposing the alcohol or not.

Firstly, a bacterial solution containing the *Bacillus coagulans* TCI711 (called as 1OD bacterial solution hereafter) realizing $OD_{600}=1$ OD (1 OD=$5\times10^8$ CFU) was prepared from the secondarily activated bacterial solution prepared in Experiment 1 and the MRS culture medium. $OD_{600}$ was an optical density (OD value) determined by an ELISA reader at a wavelength of 600 nm.

For Experiment group, a 5%-alcohol-containing MRS culture medium was inoculated with 1% (v/v) of 1OD bacterial solution. For Control group, a 5%-alcohol-containing MRS culture medium (not inoculated with the *Bacillus coagulans* TCI711) with the same total quantity was directly used. Then, Control group and Experiment group were put into the same environment to be cultured for 8 h at a temperature of 37° C. Herein, the MRS culture medium was purchased from BD Difco™.

Then, after each group was cultured, the formed bacterial solution was collected into a centrifuge tube for centrifugation. After the centrifugation, supernatants were collected. Then, the collected supernatants were distilled for 1 h at a temperature in a range of 60° C. to 80° C., and its condensing liquid was collected. Finally, an alcohol degree (W/W %) of condensed solution was measured by a graduated alcoholometer (Model: AL80).

Figure 5:
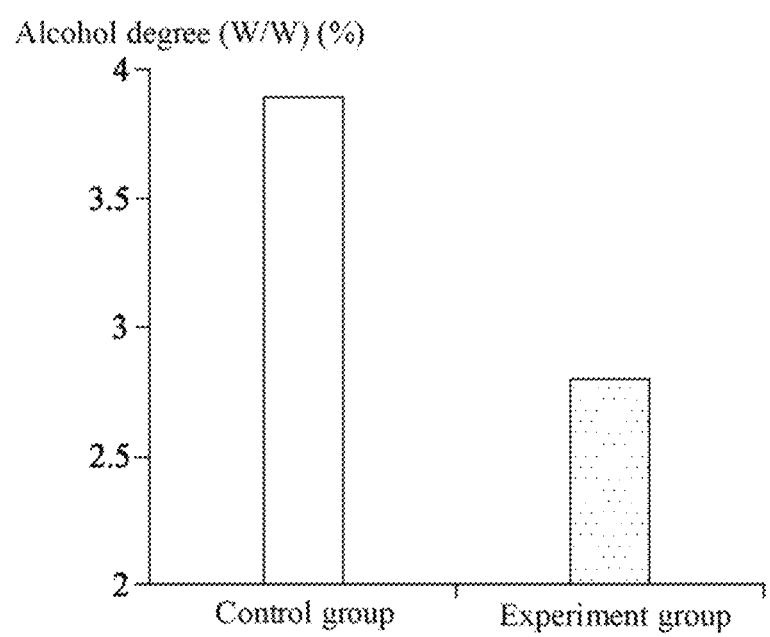
FIG. 5 is a diagram of a result of an alcohol metabolizing experiment of *Bacillus coagulans* TCI711.

Referring to FIG. 5, the alcohol degree measured by Control group was 3.9% (w/w). The alcohol degree of Experiment group was reduced to a value below 2.8%. In other words, in comparison with Control group, the *Bacillus coagulans* TCI711 could reduce 28% of the alcohol content within 8 h. Based on the above, the *Bacillus coagulans* TCI711 had the effect of directly metabolizing the alcohol.

Experiment 5: Thallus Protein Analysis

Firstly, an initial bacterial solution realizing $OD_{600}=0.1$ OD was prepared from the secondarily activated bacterial solution prepared in Experiment 1 and the MRS culture medium. The initial bacterial solution was cultured over the night in a 37° C. anaerobic environment, so as to obtain a to-be-tested bacterial solution realizing $OD_{600}=8$ OD.

The to-be-tested bacterial solution was centrifuged for 20 min by a high-speed centrifuge (Heraeus™ Megafuge™ 16 centrifuge, Thermo Scientific™) at a rotating speed of 5,000 XP. Then, supernatants were removed, and precipitates (i.e., thalli) remained. Then, the thalli were re-dissolved by 50 mL of lysis buffer solution. Next, 1 μg/ml DNAse was added. Reaction was performed at a room temperature for 10 min, so as to form a to-be-broken bacterial solution. Herein, the lysis buffer solution was prepared from 50 mM $NaH_2PO_4$, 300 mM NaCl and 1 mM $MgCl_2$, and its pH was 7.

After reaction, the to-be-broken bacterial solution was respectively subjected to three times of bacterium breaking by a high-pressure bacterium breaking machine (Constant System TS series CF1) at three kinds of pressures of 25 Kpsi, 30 Kpsi and 32 Kpsi so as to obtain a bacterium breaking solution.

The bacterium breaking solution was dried for 24 h by a freeze-drying machine (EYELA®) in a −80° C. low-temperature and vacuum environment. The moisture in the bacterium breaking solution was removed in a mode of being directly sublimated into water vapor, so as to obtain dried broken bacteria.

Then, the dried broken bacteria were prepared into a 30 mg/ml sample by using acetonitrile and trifluoroacetic acid as solvents. The sample was separated by a high performance liquid chromatograph by setting a detection wavelength to be 220,280 nm, a flow rate to be 0.5 m/min, a column temperature to be 40° C., a sample feeding volume to be 20 μL, and a gradient setting ACN to be 0% to 45%. Separated peptide fractions were dried for 24 h by the freeze-drying machine (EYELA®) at a −80° C. low-temperature and vacuum environment to obtain coarsely separated peptides.

After the coarsely separated peptides were re-dissolved by 300 μL of sterile water, 10 μL of coarsely separated peptide water solution was taken out and separated by a nanometer liquid chromatograph (UltiMate™ 3000 RSLCnano LC Systems). Then, the molecular mass of the separated peptides was analyzed through a time-of-flight tandem mass spectrometer system (Q-TOF Mass Spectrometry: TripleTOF® 6600 System). The mass was compared to NCBI and UniProt databases. A result including a 50S ribosomal protein, a small acid-soluble spore protein, a 30S ribosomal protein, an elongation factor Tu, glyceraldehyde-3-phosphate, aldehyde dehydrogenase, an uncharacterized protein, ornithine aminotransferase, a ribosome hibernation promoting factor, short-chain dehydrogenase, Pfp1 family intracellular protease, succinate CoA ligase, dihydrolipoamide acetyltransferase, 3-oxoacyl-[acyl-carrier protein] reductase, a UPF0180 protein HMPREF3212_01356, a late embryogeneis abundant protein, glucokinase, fructose-1,6-bisphosphatase, dihydrolipoyllysine-residue, a cold shock protein CspB, aldolase 2, and alcohol dehydrogenase could be obtained, as shown in FIG. 6.

Figure 6:
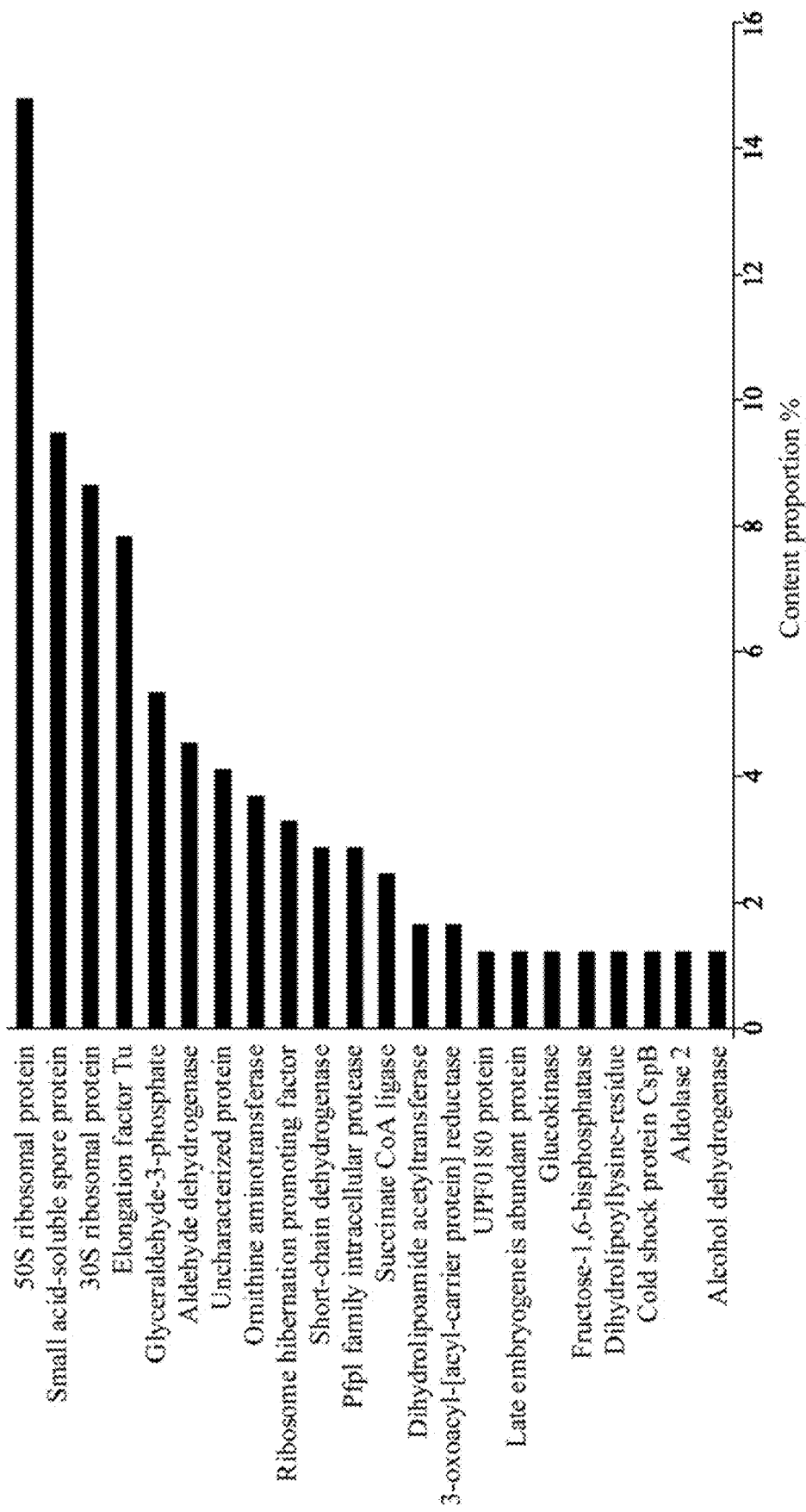
FIG. 6 is a diagram of a result of ingredient and content analysis of *Bacillus coagulans* TCI711.

Referring to FIG. 6, in the *Bacillus coagulans* TCI711, the material with the highest content was the SOS ribosomal protein. The content of the SOS ribosomal protein relative to the total protein content of the *Bacillus coagulans* TCI711 was 14.8%. The material with the secondly highest content was the small acid-soluble spore protein. The content of the small acid-soluble spore protein relative to the total protein content of the *Bacillus coagulans* TCI711 was 9.47%. In the rest proteins, the content of the 30S ribosomal protein is 8.64%, the content of the elongation factor Tu is 7.82%, the content of the glyceraldehyde-3-phosphate is 5.35%, the content of the uncharacterized protein was 4.12%, the content of the ornithine aminotransferase was 3.7%, the content of the ribosome hibernation promoting factor was 3.29%, the content of the short-chain dehydrogenase was 2.88%, the content of the Pfp1 family intracellular protease was 2.88%, the content of the succinate CoA ligase was 2.47%, and the content of the dihydrolipoamide acetyltransferase and the 3-oxoacyl-[acyl-carrier protein] reductase was 1.65%. The content of the UPF0180 protein, the late embryogeneis abundant protein, the glucokinase, the fructose-1,6-bisphosphatase, the dihydrolipoyllysine-residue, the cold shock protein CspB and the aldolase 2 was 1.23%.

Additionally, the *Bacillus coagulans* TCI711 further included the alcohol dehydrogenase accounting for more than 1.23% of the total protein content of the *Bacillus coagulans* TCI711 and the aldehyde dehydrogenase accounting for 4.53% of the total protein content of the *Bacillus coagulans* TCI711. The alcohol dehydrogenase was used for converting the alcohol into acetaldehyde, and the aldehyde dehydrogenase was used for converting acetaldehyde into acetic acid.

Through this result, it could be known that the *Bacillus coagulans* TCI711 included the protein relevant to alcohol metabolism, so that the alcohol could be directly metabolized in the intestinal tract.

Experiment 6: Human Body Experiment

Herein, a human body experiment was performed so as to confirm the practical influence of taking the *Bacillus coagulans* TCI711 on the sobering up efficacies on the human bodies. Experiment included Control group and Experiment group. Each group respectively included 5 subject.

Control group: Subjects not taking the *Bacillus coagulans* TCI7M drunk 75 mL of drinkable brewed wine (Jack Daniel's Bourbon Whisky) with an alcohol concentration of 40% within 30 min after the meal. Then, alcohol values of each subject were respectively detected by an alcometer (LION Alcometer® 400) at 5 detection points of 0 min (test was immediately performed after drinking), 30 min, 60 min, 90 min and 120 min.

Experiment group: Subjects took *Bacillus coagulans* TCI711 capsules after the meal every day (i.e., $1\times10^{10}$ cells of the *Bacillus coagulans* TCI711 were taken every day) continuously for 1 week. Then, 75 mL of drinkable brewed wine with an alcohol concentration of 40% was drunk within 30 min after the capsule taking on the last day. Then, alcohol values of each subject were respectively detected by an alcometer (LION Alcometer® 400) at the above 5 detection points. Herein, the *Bacillus coagulans* TCI711 in the capsules was taken from the secondarily activated bacterial solution prepared in Experiment 1.

Herein, mean values of the alcohol values of the five subjects in the same group and at the same detection point were taken so as to obtain a test result (as shown in Table 1 below and FIG. 7).

TABLE 1

|  | 0 min | 30 min | 60 min | 90 min | 120 min |
| --- | --- | --- | --- | --- | --- |
| Control group (mg/L) | 0.192 | 0.092 | 0.062 | 0.048 | 0.026 |
| Experiment group (mg/L) | 0.118 | 0.030 | 0.024 | 0.006 | 0.000 |

Figure 7:
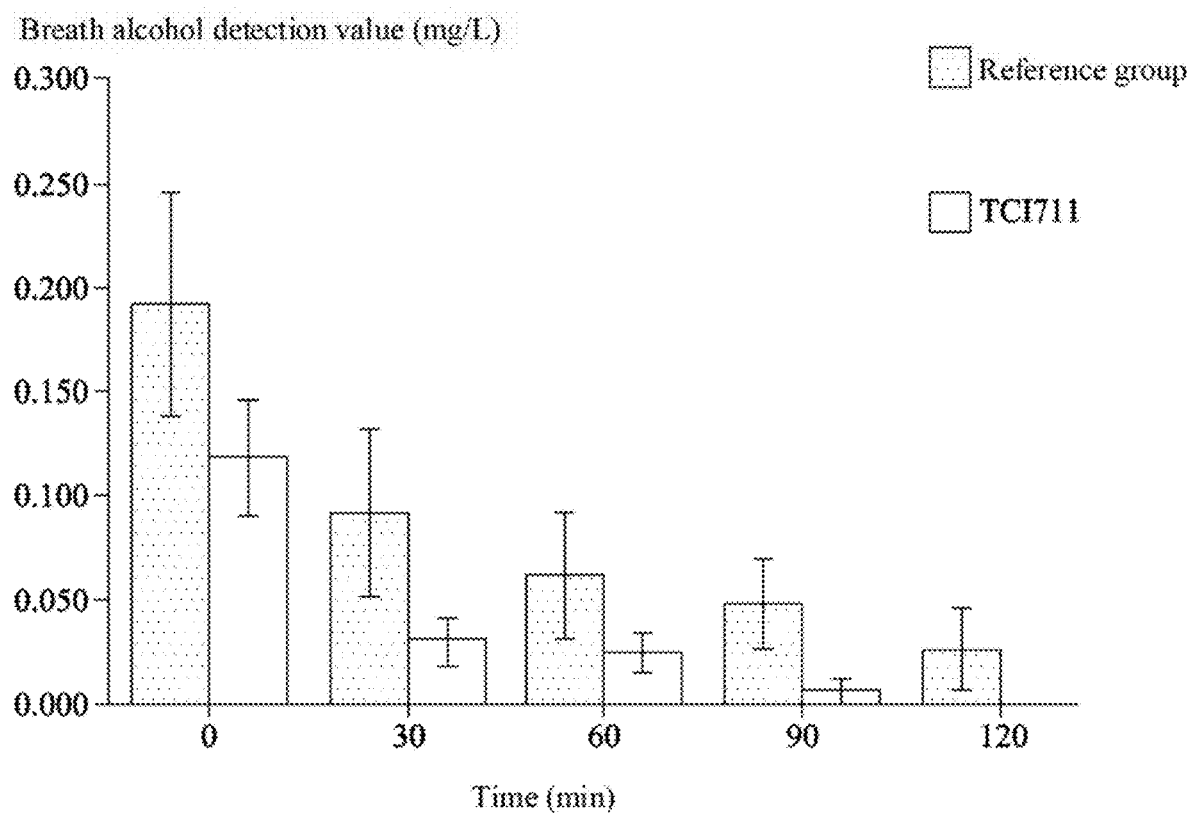
FIG. 7 is a diagram of a result of a human body alcohol metabolizing experiment of *Bacillus coagulans* TCI711.

Referring to Table 1 and FIG. 7, at 0 min after alcohol drinking, the alcohol degree of Experiment group was obviously lower than that of Control group. Therefore, it could be known that the absorption degree of the subjects taking the *Bacillus coagulans* TCI711 on the alcohol was reduced. That is, a protection layer had been formed on the intestinal wall of the subjects continuously taking the *Bacillus coagulans* TCI711 for a week, and the efficacy of directly decomposing the alcohol and reducing the alcohol absorption was realized.

At 90 min after the alcohol drinking, the alcohol value of Experiment group had been approaching to 0. That is, within 90 min after the alcohol drinking, the *Bacillus coagulans* TCI711 almost completely decomposed the alcohol in the bodies of the subjects. At 120 min after the alcohol drinking, the alcohol value of Experiment group had been 0 mg/L, that showed that within 2 h after the alcohol drinking, the *Bacillus coagulans* TCI711 had completely decomposed the alcohol in the bodies of the subjects. That is, the subjects continuously taking the *Bacillus coagulans* TCI711 for a week could faster metabolize the alcohol in the bodies than the subjects not taking the *Bacillus coagulans* TCI711.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method of sobering up of a human subject who has consumed alcohol, the method comprising administering to the human subject a composition comprising an effective dose of *Bacillus coagulans* TCI711, where the *Bacillus coagulans* TCI711 is deposited in Microbial and Cell Culture Collection Center Deutsche Sammlung von Mikroorganismen und Zellkulturen GmbH (DSMZ) under the deposit number DSM33163.

2. The method according to claim 1, wherein the *Bacillus coagulans* TCI711 achieves a sobering up function by directly metabolizing the alcohol consumed by the human subject.

3. The method according to claim 2, wherein the *Bacillus coagulans* TCI711 metabolizes the alcohol through its alcohol dehydrogenase and aldehyde dehydrogenase.

4. The method according to claim 1, wherein the *Bacillus coagulans* TCI711 reduces alcohol absorption by 38.7% as compared to that in a human subject not administered with the composition, by forming a protection film on the intestinal wall so as to achieve the sobering up function.

5. The method according to claim 2, wherein the *Bacillus coagulans* TCI711 has acid-alkali tolerance ranging from pH 3 to pH 7.

6. The method according to claim 2, wherein the *Bacillus coagulans* TCI711 has an intestinal tract colonization rate of 346 CFU per intestinal tract cell.

7. The method according to claim 2, wherein the effective dose is $1\times10^{10}$ cells/day.

* * * * *